United States Patent
Foley et al.

(10) Patent No.: US 10,696,605 B2
(45) Date of Patent: Jun. 30, 2020

(54) USES OF VANADIUM TO OXIDIZE ALDEHYDES AND OZONIDES

(71) Applicant: P2 SCIENCE, INC., Woodbridge, CT (US)

(72) Inventors: Patrick Foley, New Haven, CT (US); Yonghua Yang, New Haven, CT (US); Tania Salam, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 16/333,677

(22) PCT Filed: Sep. 15, 2017

(86) PCT No.: PCT/US2017/051817
§ 371 (c)(1),
(2) Date: Mar. 15, 2019

(87) PCT Pub. No.: WO2018/053289
PCT Pub. Date: Mar. 22, 2018

(65) Prior Publication Data
US 2019/0225558 A1    Jul. 25, 2019

Related U.S. Application Data

(60) Provisional application No. 62/395,455, filed on Sep. 16, 2016.

(51) Int. Cl.
| | |
|---|---|
| C07C 45/00 | (2006.01) |
| C07C 51/34 | (2006.01) |
| B01J 23/00 | (2006.01) |
| C07B 41/08 | (2006.01) |
| B01J 23/22 | (2006.01) |
| C07C 53/126 | (2006.01) |
| C07C 51/235 | (2006.01) |
| C07C 45/40 | (2006.01) |
| C07B 33/00 | (2006.01) |
| C07C 49/17 | (2006.01) |
| C07C 59/01 | (2006.01) |

(52) U.S. Cl.
CPC .............. *C07B 41/08* (2013.01); *B01J 23/22* (2013.01); *C07B 33/00* (2013.01); *C07C 45/40* (2013.01); *C07C 49/17* (2013.01); *C07C 51/235* (2013.01); *C07C 51/34* (2013.01); *C07C 53/126* (2013.01); *C07C 59/01* (2013.01); *Y02P 20/127* (2015.11)

(58) Field of Classification Search
CPC ....... C07C 45/40; C07C 51/34; C07C 51/235; B01J 23/22
See application file for complete search history.

(56) References Cited

U.S. PATENT DOCUMENTS

| | | |
|---|---|---|
| 2,813,113 A | 11/1957 | Goebel et al. |
| 3,023,244 A | 2/1962 | Eschinasi |
| 3,699,169 A | 10/1972 | Bertele et al. |
| 4,296,258 A | 10/1981 | Fehr et al. |
| 4,311,617 A | 1/1982 | Ansari et al. |
| 4,491,537 A | 1/1985 | Futoshi et al. |
| 4,791,228 A | 12/1988 | Siclari et al. |
| 4,940,808 A | 7/1990 | Schulz et al. |
| 5,292,941 A | 3/1994 | Kigawa et al. |
| 5,543,565 A | 8/1996 | McVay et al. |
| 5,756,821 A | 5/1998 | Dilk et al. |
| 5,801,275 A | 9/1998 | McVay et al. |
| 6,309,521 B1 | 10/2001 | Andrews et al. |
| 6,395,695 B1 | 5/2002 | Sivik |
| 6,512,131 B1 | 1/2003 | Best et al. |
| 6,545,186 B2 | 4/2003 | Giselbrecht et al. |
| 6,548,715 B1 | 4/2003 | Bouillion et al. |
| 7,825,277 B2 | 11/2010 | Gutsche et al. |
| 7,968,742 B2 | 6/2011 | Aigner et al. |
| 8,221,708 B2 | 7/2012 | Seebauer et al. |
| 9,035,091 B2 | 5/2015 | Foley et al. |
| 9,604,898 B2 | 3/2017 | Foley et al. |
| 9,682,914 B2 | 6/2017 | Foley et al. |
| 9,701,606 B2 | 7/2017 | Goeke et al. |
| 10,011,582 B2 | 7/2018 | Foley et al. |
| 10,071,944 B2 | 9/2018 | Foley et al. |
| 10,280,131 B2 | 5/2019 | Foley et al. |
| 2003/0078453 A1 | 4/2003 | Springer et al. |
| 2003/0100781 A1 | 5/2003 | Springer et al. |
| 2004/0186042 A1 | 9/2004 | Schmaus et al. |
| 2007/0010688 A1 | 1/2007 | Ko et al. |
| 2007/0142666 A1 | 6/2007 | Himeno et al. |

(Continued)

FOREIGN PATENT DOCUMENTS

| | | |
|---|---|---|
| CA | 1144561 | 4/1983 |
| CN | 102653531 A | 9/2012 |

(Continued)

OTHER PUBLICATIONS

English Abstract of Japanese Publication No. H06-135878, published May 17, 1994.

(Continued)

*Primary Examiner* — Sikarl A Witherspoon
(74) *Attorney, Agent, or Firm* — Hoxie & Associates LLC (57) ABSTRACT

The present invention relates to uses of vanadium to convert aldehydes and ozonides into their respective acids and/or ketones. More particularly, this invention relates to the oxidative work-ups following ozonolysis using vanadium during ozonolysis, and using vanadium to oxidize aldehydes in general. The invention also relates to methods comprising the ozonolysis of oleyl alcohol in the presence of either an acid or an alcohol.

21 Claims, 3 Drawing Sheets

(56) References Cited

U.S. PATENT DOCUMENTS

| | | |
|---|---|---|
| 2007/0276165 A1 | 11/2007 | Gutsche et al. |
| 2009/0221083 A1 | 9/2009 | White et al. |
| 2013/0078685 A1 | 3/2013 | Ulrich et al. |
| 2013/0177497 A1 | 7/2013 | Fitch et al. |
| 2013/0338150 A1 | 12/2013 | Boehme et al. |
| 2014/0316149 A1 | 10/2014 | Wickens et al. |
| 2015/0183707 A1 | 7/2015 | Foley et al. |
| 2017/0247314 A1 | 8/2017 | Foley et al. |
| 2017/0275230 A1 | 9/2017 | Foley et al. |

FOREIGN PATENT DOCUMENTS

| | | |
|---|---|---|
| CN | 102795987 A | 11/2012 |
| EP | 0555472 A1 | 8/1993 |
| EP | 0761629 A1 | 3/1997 |
| EP | 1860093 A1 | 11/2007 |
| JP | H06-135878 | 5/1994 |
| WO | WO 1995/001960 | 1/1995 |
| WO | WO 2002/048431 | 6/2002 |
| WO | WO 2007/068498 | 6/2007 |
| WO | WO 2009/061806 | 5/2009 |
| WO | WO 2012/177357 | 12/2012 |
| WO | WO 2013/053102 | 4/2013 |
| WO | WO 2015/039010 | 3/2015 |
| WO | WO 2015/106293 | 7/2015 |
| WO | WO 2015/126936 | 8/2015 |
| WO | WO 2015/191706 | 12/2015 |
| WO | WO 2015/196019 | 12/2015 |
| WO | WO 2016/091895 | 6/2016 |
| WO | WO 2017/223220 | 12/2017 |
| WO | WO 2018/053289 | 3/2018 |

OTHER PUBLICATIONS

Abe, et al, "Synthesis of Massoia lactone and its analogs. I. Synthesis of the lactone of 1-decen-4-ol-1-carboxylic acid," 75 Nippon Kagaka Kaishi, Pure Chem., 953-5, (1921-1947), (1954). [CAS Abstract Only].

Avdeev, et al., "Molecular Mechanism of Oxygen Isotopic Exchange over Supported Vanadium Oxide Catalyst Vox/TiO2," *The Journal of Physical Chemistry C*, vol. 117, No. 6, pp. 2879-2887, (2013).

Ayer, et al., "Degraded Monoterpenes from the Opisthobranch Mollusc *Melibe leonina*," Short Communications, Experientia 39, Birkhauser Verlag, CH-4010 Basel/Switzerland, (1983), 2 pages.

Cermak, et al., "Synthesis of δ-Stearolactone from Oleic Acid," *JAOCS*, vol. 77, No. 3, pp. 243-248, (2000).

Chen, et al., "A Predictably Selective Aliphatic C—H Oxidation Reaction for Complex Molecule Synthesis," *Science*, vol. 318, (2007).

Chmielewski, et al., "Organic Syntheses Under High Pressure. 3. General Approach to the Synthesis of Naturally Occuring .delta.-lactones," *The Journal of Organic Chemistry*, vol. 46, No. 11, pp. 2230-2233, (1981).

"Aliphatic Carboxylic Acids," Competition Science Vision Aug. 2000, *Pratiyogita Darpan*, vol. 3, No. 30, pp. 799. [ 2 pages].

Cook, et al., "Study of the Total Synthesis of (−)-Exiguolide," *J. Org. Chem.*,vol. 77, pp. 6728-6742, (2012).

Cullen, William, "Re: Melibe from Alaska," Jan. 12, 2001, Australian Museum, Sydney, pp. 1-4.

Dupe, et al., "Methyl Ricinoleate as Platform Chemical for Simultaneous Production of Fine Chemicals and Polymer Precursors," *ChemSusChem.*, vol. 5, pp. 2249-2254, (2012).

Förtsch, et al., "Synthese, Kristallstruktur und Reaktionen neuartiger metallacyclischer Dioxo- und Aminooxocarben-Komplexe des Eisens," *Chem. Ber.*, vol. 127, pp. 711-715, (1994). [English Abstract Only.].

Gerth, et al., "Synthesis of δ-Lactones via Radical C—C Bond Formation Using Chiral Radical Precursors," *J. Org. Chem.*, vol. 51, pp. 3726-3729, (1986).

Gross, R.A., Jr., "Ozonolysis Problems That Promote Student Reasoning," *Journal of Chemical Education*, vol. 83, No. 4, pp. 604-609, (2006).

Harding, et al., "beta-Methyl-delta-dodecadiene and beta-Methyl-delta-decadiene," *Journal of the Chemical Society*, Transactions, pp. 448-451, (1911).

Hearn, et al., "Kinetics and Product Studies for Ozonolysis Reactions of Organic Particles Using Aerosol CIMS," *The Journal of Physical Chemistry A*, vol. 108, No. 45, pp. 10019-10029, (2004).

Kadesch, R.G., "Ozonolysis of Fatty Acids and Their Derivatives," *Progress in the Chemistry of Fats and Other Lipids*, vol. 6, pp. 291-312, (1963).

Kauffmann, et al., "Ubergangsmetallaktivierte organische Verbindungen, XXXVIII. Chemoselektive nucleophile Methylierungen durch In-Situ-Blockierung von Aldehydgruppen unter [alpha]1-Phosphonioalkoxid-Bildung," *Chemishe Berichte*, pp. 459-464, (1993). [No English Translation.].

Kula, et al., "Synthesis of Enantiomerically Pure Volatile Compounds Derived From (R)-3-Hydroxynonanal," *Tetrahedron: Asymmetry*, vol. 11, pp. 943-950, (2000).

Lee, et al., "Tin-free, Radical-mediated Gamma-alkylations of Alpha, Beta-unsaturated Esters via O-tert-alkyl Dienol Ethers," vol. 1, pp. 49-54, (2008).

Maggiolo, A. "Ozonization of Fatty Acids and Their Derivatives," *The Journal of the American Oil Chemists' Society*, vol. 40, pp. 161-164, (1963).

Otsubo, et al., "A Direct Synthesis of [gamma]-, [delta], and [epsilon]—Lactones Utilizing SmI2-induced Barbier-type Reaction in the Presence of Hexamethylphosphoric Triamide (HMPA)," *Chemistry Letters*, pp. 1487-1490, (1987). Http://www.journal.csj.jp/doi/pdf/10.1246/c1.1987.1487 [retrieved on May 29, 2017].

PubChem-CID-107500001, Oct. 26, 2006, 17 pages.

Quan, et al., "A Convenient Protecting Group for Aldehydes," *Synlett*, vol. 2001, No. 12, pp. 1925-1926, (2001).

Rani, et al., "Ozonolysis of Oleic Acid Over a Nano Vanadium Pentoxide (V2O5) Catalyst," *European Journal of Scientific Research*, vol. 24, No. 3, pp. 428-432, (2008).

Richardson, et al., "A Practical Synthesis of Long-Chain Iso-Fatty Acids (iso-C 12-C19) and Related Natural Products," *Beilstein Journal of Organic Chemistry*, vol. 9, pp. 1807-1812, (2013).

Rosenberger, et al., "28. Synthesis of δ-Lactones From Glutaraldehyde," *Helvetica Chimica Acta*, vol. 55, pp. 249-255, (1972).

Sabitha, et al., "The First Asymmetric Total Synthesis of (R)-Tuberolactone, (S)-Jasmine Lactone, and (R)-δ-Decalactone," *Tetrahedron Letters*, vol. 47, pp. 8179-8181, (2006).

Schiaffo, C.E., "I. An Improved Procedure for Alkene Ozonolysis. II. Expoloring a New Structural Paradigm for Peroxide Antimalarials," *Student Research Projects, Dissertations, and Theses—Chemistry, Department, University of Nebraska-Lincoln*, (Jun. 2011), Paper 23.

Shao, et al., "Asymmetric Hydrogenation of 3,5-Dioxoesters Catalyzed by Ru-binap Complex: A Short Step Asymmetric Synthesis of 6-Substituted 5,6-dihyrdo-2-pyrones," *Tetrahedron*, vol. 49, No. 10, pp. 1997-2010, (1993).

Shekhter, et al., "Study of Compounds with Juvenile-hormone Activity. X. Synthesis of Esters of 2E,4E-3,11-dimethyl-11-methoxy-2,4-dodecadienic and 2E,4E-2, 11-dimethyl-2,4,10-dodecatrienic acids," *Zhurnal Organicheskoi Khimii*, vol. 15, No. 2, pp. 260-264, (1979).

Shono, et al., "Electroreductive Intermolecular Coupling of Ketones with Olefins," *J. Org. Chem.*, vol. 54, No. 26, pp. 6001-6003, (1989).

STN 1984 (Year: 1984), p. 1.
STN Nov. 1984 (Year: 1984), 1 Page.
STN 1995 (Year: 1995), 1 Page.
STN Sep. 29, 2005 (Year: 2005), 1 Page.
STN Mar. 7, 2013 (Year: 2013), 1 Page.

Surburg, et al., *Common Fragrance and Flavor Materials*, 5th Ed. Wiley-VCH, pp. 149-172, (2006).

Tanaka, et al., "Syntheses of (5E)-PGE2 and New 6-Functionalized Derivatives by the Use of Palladium-Catalyzed Decarboxylative Allylic Alkylation," *Tetrahedron*, vol. 42, No. 24, pp. 6747-6758, (1986).

Utaka, et al., "New Synthesis of Jasmine Lactone and Related-δ-Lactones from 1,2 Cyclohexanedione. Preparation and Dye- (56) References Cited

OTHER PUBLICATIONS

Sensitized Photooxygenation of 3-(2-Alkenyl)- and 3-(2-Alkynyl)-1,2-cyclohexanediones," *J. Org. Chem.*, vol. 51, No. 6, pp. 935-938, (1986).

Wasmi, et al, "Synthesis of Vanadium Pentoxide Nanoparticles as Catalysts for the Ozonation of Palm Oil," *Ozone: Science & Engineering*, vol. 38, No. 1, pp. 36-41, (2015).

Willand-Charnley, et al., "Pyridine is an Organocatalyst for the Reactive Ozonolysis of Alkenes," *Org. Lett.*, vol. 14, No. 9, pp. 2242-2245, (2012).

Written Opinion of the International Searching Authority for International Application No. PCT/US2017/051817 dated Dec. 8, 2017, 9 pages.

Yahata, et al., "Methodology for in Situ Protection of Aldehydes and Ketones Using Trimethylsilyl Trifluoromethanesulfonate and Phosphines: Selective Alkylation and Reduction of Ketones, Esters, Amides, and Nitriles," *Chem. Pharm. Bull.*, vol. 61, No. 12, pp. 1298-1307.

USES OF VANADIUM TO OXIDIZE ALDEHYDES AND OZONIDES

CROSS-REFERENCE TO RELATED APPLICATIONS

This application is a U.S. National Stage application filed under 35 U.S.C. § 371 of International Application No. PCT/US2017/051817, filed Sep. 15, 2017, which claims the benefit of and priority from U.S. Provisional Application 62/395,455, filed on Sep. 16, 2016, the entire contents of each of which are incorporated herein by reference in their entireties.

FIELD OF THE INVENTION

The present invent relates to uses of vanadium to convert aldehydes and ozonides into their respective acids and/or ketones. More particularly, this invention relates to the oxidative work-ups following ozonolysis using vanadium, using vanadium during ozonolysis, and using vanadium to oxidize aldehydes in general.

BACKGROUND OF THE INVENTION

The oxidation of aldehydes to acids is of broad synthetic and industrial interest, with brassylic acid and azelaic acid production from vegetable oils requiring this transformation (see U.S. Pat. No. 5,543,565), as well as maleic acid production from crotonaldehyde. This latter transformation requires the reaction to be at very high temperatures in the gaseous phase.

Fine chemical and commodity chemical production methods that incorporate oxidization of aldehydes have lacked a certain amount of safety, are expensive, are relatively inefficient and lack a desirable purity profile. Consequently there is a need for an inexpensive, efficient, and safe method to oxidize aldehydes on any type of production scale.

SUMMARY OF THE INVENTION

The current invention encompasses the surprising discovery that under certain defined methods, similar aldehydes can be oxidized at very moderate temperatures, using trace amounts of catalyst (e.g., vanadium), and using air or oxygen to regenerate the catalyst. Further, the conditions described herein can result in very fast and clean conversions of peroxide, ozonide, and aldehyde to their corresponding oxidized states. These conditions can be applied broadly to both fine chemical and commodity chemical production.

In still another aspect, this invention relates to use of oxidative ozonolysis to generate valuable monomers from plant-derived fatty alcohols, specifically oleyl alcohol. In this aspect, the oxidation can occur using trace amounts of catalyst (e.g., vanadium)

The following discloses a simplified summary of the specification in order to provide a basic understanding of some aspects of the specification. This summary is not an extensive overview of the specification. It is intended to neither identify key or critical elements of the specification nor delineate the scope of the specification. Its sole purpose is to disclose some concepts of the specification in a simplified form as to prelude to the more detailed description that is disclosed later.

DETAILED DESCRIPTION OF THE INVENTION

Solutions of aldehyde either neat or in an organic acid such as acetic acid (10-50% by wt. aldehyde generally) can be charged with very small amounts—substantially less than 0.5% by wt. with respect to aldehyde—of $V_2O_5$ as a fine yellow orange solid. The solution can then be kept at room temperature or heated in the presence of an air stream or oxygen gas stream sparging through the liquid, and can be used with any of Method 1, et seq, Method 2, et seq, Method 3, et seq, or Method 4, et seq. These conditions generally allow for rapid and clean conversion of aldehyde to carboxylic acid. It is noted that other acidic solvent systems, such as propanoic or nonanoic acid could be used, or classic organic solvents in conjunction with acid, and other temperatures and concentrations could also be considered. Further, other gas introduction methods such as jet injection, film contacting, rapid stirring, or aerosol misting could also be considered, depending upon embodiment, and can be used with any of Method 1, et seq, Method 2, et seq, Method 3, et seq, or Method 4, et seq.

It was surprisingly found that aldehydes can be oxidized using vanadium pentoxide ($V_2O_5$). In certain aspects this can involve the use of a solvent (e.g., acetic acid) and using either air or oxygen as a gas to regenerate the catalyst. In certain aspects, the reaction can take place at temperatures ranging from room temperature to about 110° C. In certain aspects reactions are largely completed in less than 4 hours and a wide variety of aldehydes can be oxidized under these conditions.

In one aspect the invention encompasses Method 1.0, wherein an aldehyde is oxidized using vanadium (e.g., vanadium pentoxide ($V_2O_5$)) as a catalyst, wherein the Method comprises the following:

In certain aspects, Method 1.0 can encompass the following:
1.1 The method of Method 1, wherein said temperature range is between 10° C. and 150° C.
1.2 The method of Method 1.1, wherein said temperature range is between 20 and 120° C.
1.3 The Method of Method 1.2, wherein the oxidation occurs at between 20 and 110° C.
1.4 The Method of any of the preceding methods, wherein the oxidation occurs at 20° C., 30° C., 40° C., 50° C., 60° C., 70° C., 80° C., 90° C., 100° C., or 110° C.
1.5 The Method of any of the preceding methods, wherein the oxidation occurs at about 60° C.
1.6 The method of any of the preceding methods, wherein the catalyst is vanadium pentoxide ($V_2O_5$).
1.7 The Method of any of the preceding Methods, wherein the aldehyde is diluted in an organic solvent.
1.8 The Method of 1.7, wherein the organic solvent may be acetic acid, nonanoic acid, propanoic acid, palmitic acid, myristic acid, lauric acid, octanoic acid, methanol, isopropanol, ethanol, or mixtures thereof.

1.9 The Method of any of the preceding Methods, wherein a cationic exchange resin can be used to facilitate the reaction.

1.10 The Method of any of the preceding Methods, wherein the cationic exchange catalyst is selected from Silicycle propanesulfonic acid, montmorillonite, or Amberlyst® (e.g., macroreticular or cellular resins or silica covalently bonded to sulfonic acid or carboxylic acid groups).

1.11 The Method of any of the proceeding Methods, wherein the aldehyde, without limitation, can be selected from the group consisting of: alkyl aldehydes such as formaldehyde, ethanal, propanal, butanal, pentanal, hexanal, heptanal, octanal, nonanal and decanal, as well as their isomers and oxo analogs. Branched and functionalized acids such as citronellal, hydroxyciitronellal, methoxymelonal, hydroxymelonal, melonal, and methoxycitronellal can also be oxidized this way.

1.12 The method of any of the preceding methods, wherein the aldehyde is selected from the group consisting of: aliphatic aldehydes (e.g., acetaldehyde, octanal, nonanal, decanal, undecanal, 2,6-dimethyl-5-heptanal, 3,5,5-trimethylhexanal, cis-3, cis-6-nonadienal, trans-2, cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.); aromatic aldehydes (anisic aldehyde, a-amylcinnamic aldehyde, a-methylcinnamic aldehyde, cyclamen aldehyde, p-isopropylphenylacetaldehyde, ethylvanillin, cumin aldehyde, salicylaldehyde, cinnamic aldehyde, 0-, m- or p-tolylaldehyde, vanillin, piperonal, phenylacetaldehyde, heliotropin, benzaldehyde, 4-methyl-2-pheny-2-pentenal, p-methoxy cinnamic aldehyde, p-methoxybenzaldehyde, etc.); and terpene aldehydes (geranial, citral, citronellal, a-sinensal, β-sinensal, perillaldehyde, hydroxy citronellal, tetrahydrocitral, myrtenal, cyclocitral, isocyclocitral, citronellyloxyacetaldehyde, neral, a-methylenecitronellal, myracaldehyde, vemaldehyde, safranal, etc.)

1.13 The Method of any of the preceding Methods, wherein the vanadium can be selected from: $V_2O_5$, vanadium sulfate, vanadium phosphates, vanadinite, vanadyl acetylacetonate, vanadyl pyrophosphate, and other $V_2O_5$ equivalents 1.14 The Method of any of the preceding Methods, wherein the vanadium can be loaded onto solid phase substrate, e.g., sand, zeolite, or silica, and can largely immobilized this way in a fixed bed-type reactor for continuous operation.

1.15 The method of any of the preceding methods, further comprising an acidic solvent.

1.16 The method of method 1.15, wherein said acidic solvent comprises acetic acid.

1.17 The method of method 1.15 or 1.16, wherein said acidic solvent comprises a carboxylic acid selected from formic, propanoic, butanoic, pentanoic, hexanoic, heptanoic, octanoic, nonanoic, decanoic, dodecanoic, palmitic, and stearic acid.

1.18 The method of any of the preceding methods, wherein said aldehydes comprise C3 to C15 optionally functionalized linear alkyl aldehydes and said carboxylic acids comprise C3 to C15 optionally functionalized linear alkyl carboxylic acids.

1.19 The method of any of the preceding methods, wherein said aldehydes comprise C6 to C13 optionally functionalized linear alkyl aldehydes and said carboxylic acids comprise C6 to C13 optionally functionalized linear alkyl carboxylic acids.

1.20 The method of any of the preceding methods, wherein said aldehydes comprise C5 to C15 optionally functionalized branched alkyl aldehydes and said carboxylic acids comprise C3 to C15 optionally functionalized branched alkyl carboxylic acids.

1.21 The method of any of the preceding methods, wherein the aldehyde is hydroxycitronellal, and wherein the hydroxycitronellal is oxidized to hydroxycitronellic acid using the following method, wherein $V_2O_5$ is used as a catalyst:

1.22 The method of any of methods 1-1.20, wherein the aldehyde is methoxymelonal, and methoxymelonal is oxidized to methoxymelonic acid using the following method:

1.23 The method of 1.22, wherein $V_2O_5$ is used as a catalyst.

1.24 Any of the preceding methods, wherein the reaction mixture is then charged with vanadium (e.g., $V_2O_5$)

1.25 The method of 1.24, wherein that amount of vanadium is from 0.1%-0.5% by wt. with respect to the aldehyde (e.g., 0.3% by wt).

1.26 Any of the preceding methods, wherein the mixture is heated to 60° C. and then sparged with air.

1.27 Any of the preceding methods, wherein the mixture is heated anywhere from 50° C.-100° C. (e.g., 60° C.) and then sparged with oxygen.

In a further aspect the invention encompasses Method 2.0, where vanadium (e.g., $V_2O_5$) can be used to oxidize ozonides and quench peroxide, making it ideal for oxidative work-up following ozonolysis, or as a reagent to be used in conjunction with ozonolysis. Method 2.0 comprises the following In some aspects, Method 2.0 encompasses the following:
2.1 The method of Method 2, wherein said temperature range is between 10° C. and 150° C.
2.2 The method of Method 2.1, wherein said temperature range is between 20 and 120° C.
2.3 The Method of Method 2.2, wherein the oxidation occurs at between 20 and 110° C.
2.4 The Method of 2.3, wherein the oxidation occurs at 20° C., 30° C., 40° C., 50° C., 60° C., 70° C., 80° C., 90° C., 100° C., or 110° C.
2.5 The Method of 2.2, wherein the oxidation occurs at about 60° C.
2.6 The method of any of the preceding methods, wherein the catalyst is vanadium pentoxide ($V_2O_5$).
2.7 The Method of any of the preceding Methods, wherein the aldehyde is diluted in an organic solvent.
2.8 The Method of 2.7, wherein the organic solvent may be acetic acid, nonanoic acid, propanoic acid, palmitic acid, myristic acid, lauric acid, octanoic acid, methanol, isopropanol, ethanol, or mixtures thereof.
2.9 The Method of any of the preceding Methods, wherein a cationic exchange resin can be used to facilitate the reaction.
2.10 The Method of any of the preceding Methods, wherein the cationic exchange catalyst is selected from Silicycle propanesulfonic acid, montmorillonite, or Amberlyst® (e.g., macroreticular or cellular resins or silica covalently bonded to sulfonic acid or carboxylic acid groups).
2.11 The Method of any of the preceding Methods, wherein the vanadium can be selected from: $V_2O_5$, vanadium sulfate, vanadium phosphates, vanadinite, vanadyl acetylacetonate, vanadyl pyrophosphate, and other $V_2O_5$ equivalents
2.12 The Method of any of the preceding Methods, wherein the vanadium can be loaded onto solid phase substrate, e.g., sand, zeolite, or silica, and can largely immobilized this way in a fixed bed-type reactor for continuous operation.
2.13 The method of any of the preceding methods, wherein said vanadium further functions to quench peroxide and ozonide.
2.14 The method of any of the preceding methods, wherein said ozonides are derived from an unsaturated fatty monoacid, diacid, monoester, diester, diol, or an alcohol.
2.15 The method of any of the preceding methods, where the vanadium further functions to quench peroxide and ozonide.
2.16 Any of the preceding methods, wherein the reaction mixture is then charged with vanadium (e.g., $V_2O_5$)
2.17 The method of any of the preceding methods, wherein the amount of vanadium is from 0.1%-0.5% by wt. with respect to the ozonide (e.g., 0.3% by wt).
2.18 Any of the preceding methods, wherein the mixture is heated anywhere from 50° C.-100° C. (e.g., 60° C.) and then sparged with air.
2.19 Any of the preceding methods, wherein the vanadium (e.g., $V_2O_5$) can be loaded onto a solid support, e.g. sand, and the ozonide mixture can pass through a structured reactor or packed tube at a continuous flow rate at elevated temperature, and wherein the ozonide mixture can be oxidatively quenched.
2.20 Any of the preceding methods, wherein the mixture is heated anywhere from 50° C.-100° C. (e.g., 60° C.) and then sparged with oxygen.

In further aspects involving oxidizing ozonides, e.g., any of Method 2.0 et seq, vanadium can first be used to oxidize the peroxidic bonds in the ozonide or the reaction mixture to bring the peroxide value to very low values in the presence or absence of air or oxygen, preferably at elevated temperature. For example, in some aspects, an ozonide mixture can be charged with vanadium (V) oxide and heated to between 70 and 100° C. for a period less than an hour and >90% of all ozonide and peroxide can be converted or quenched. In another aspect, the vanadium can be loaded onto a solid support, e.g. sand, and the ozonide mixture can pass through a structured reactor or packed tube at a continuous flow rate at elevated temperature, and the ozonide mixture can be oxidatively quenched, resulting in a mixture of acids, aldehydes, and/or ketones. This mixture could then optionally be reacted with vanadium in the presence of air or oxygen to convert any residual aldehyde to acid.

Figure 1:
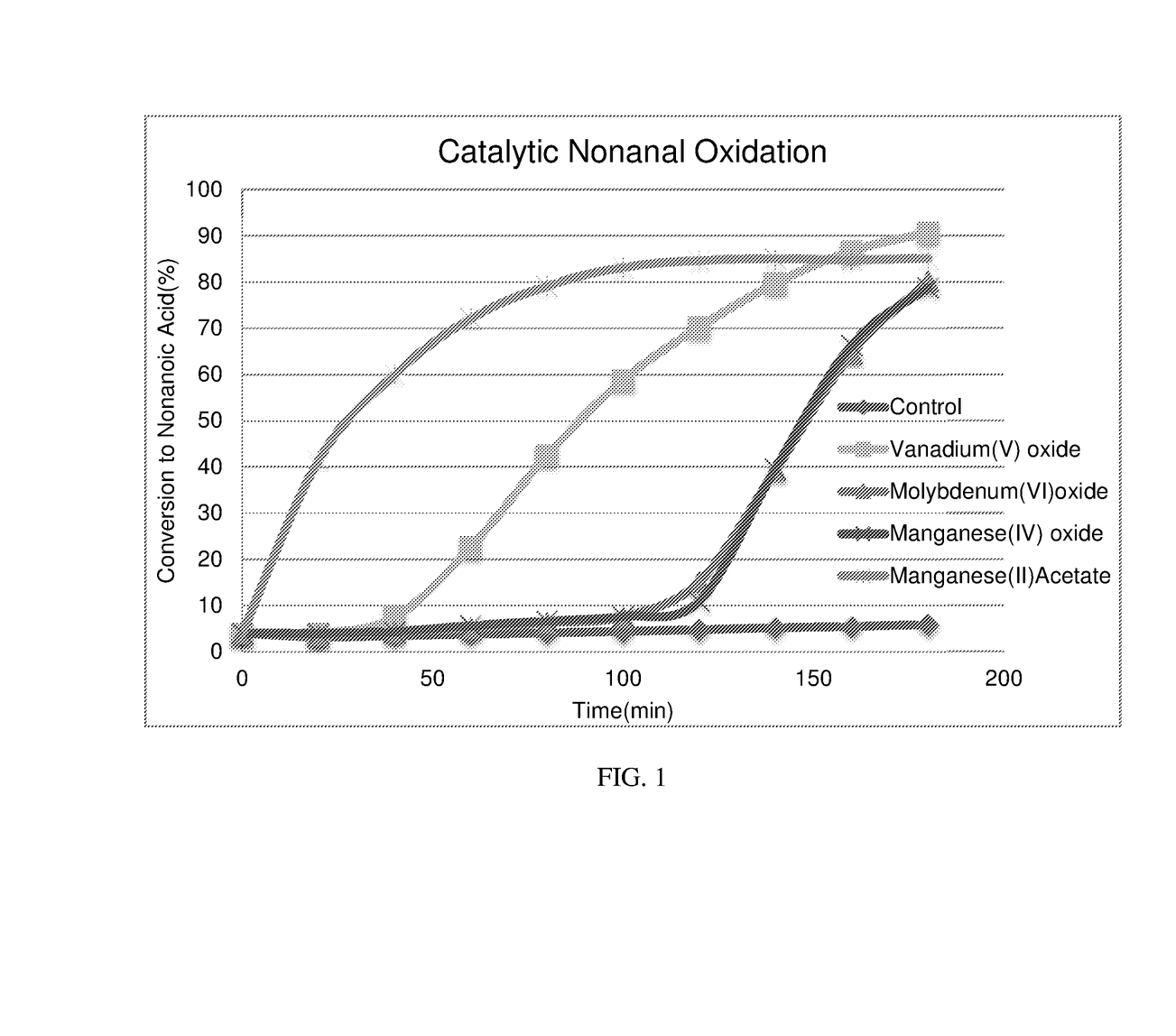
FIG. 1. The conversion of nonanal to nonanoic acid in the presence of oxygen and catalyst at elevated temperature. Standardized experimental conditions are described in Example 4 in the experimental section.

In further aspects, the Applicants surprisingly discovered that vanadium oxide resulted in superior performance in the conversion of nonanal to nonanoic acid as compared to other inorganic oxidizing catalysts. While a variety of oxidation catalysts may oxidize aldehydes, there are many byproducts that can form and undesirable discoloration can take place. Applicants discovered that after 3 hours of reaction under standardized experimental conditions, vanadium (V) oxide resulted in the cleanest and highest yielding conversion to nonanoic acid as compared to several molybdenum and manganese based oxidation catalysts. Data is demonstrated in FIG. 1.

In certain aspect, the present invention encompasses Method 3.0, which is a Method for the synthesis of nonanoic acid, wherein nonanal can be oxidized nonanoic acid:

In certain aspects, Method 3.0 encompasses the following:
3.1 The method of Method 3, wherein said temperature range is between 10° C. and 150° C.
3.2 The method of Method 3.1, wherein said temperature range is between 20 and 120° C.
3.3 The Method of Method 3.2, wherein the oxidation occurs at between 20 and 110° C.
3.4 The Method of 3.3, wherein the oxidation occurs at 20° C., 30° C., 40° C., 50° C., 60° C., 70° C., 80° C., 90° C., 100° C., or 110° C.
3.5 The Method of any of the preceding methods, wherein the oxidation occurs at about 60° C.
3.6 The method of any of the preceding methods, wherein the catalyst is vanadium pentoxide ($V_2O_5$).
3.7 The Method of any of the preceding Methods, wherein the aldehyde is diluted in an organic solvent.
3.8 The Method of 3.5, wherein the organic solvent may be acetic acid, nonanoic acid, propanoic acid, palmitic acid, myristic acid, lauric acid, octanoic acid, methanol, isopropanol, ethanol, or mixtures thereof.

3.9 The Method of any of the preceding Methods, wherein a cationic exchange resin can be used to facilitate the reaction.

3.10 The Method of any of the preceding Methods, wherein the cationic exchange catalyst is selected from Silicycle propanesulfonic acid, montmorillonite, or Amberlyst® (e.g., macroreticular or cellular resins or silica covalently bonded to sulfonic acid or carboxylic acid groups).

3.11 The Method of any of the preceding Methods, wherein the vanadium can be selected from: $V_2O_5$, vanadium sulfate, vanadium phosphates, vanadinite, vanadyl acetylacetonate, vanadyl pyrophosphate, and other $V_2O_5$ equivalents 3.12 The Method of any of the preceding Methods, wherein the vanadium can be loaded onto solid phase substrate, e.g., sand, zeolite, or silica, and can largely immobilized this way in a fixed bed-type reactor for continuous operation.

3.13 The method of any of the preceding methods, wherein the method comprises the following:

3.14 The Methods of any of the preceding Methods, further comprising mixtures of nonanal and 9-oxononanoic acid or 9-oxononanoic acid methyl ester, wherein said mixtures are oxidized to nonanoic acid and azelaic acid or azelaic acid monomethyl ester, in a Method comprising the following:

3.15 Any of the preceding methods, wherein the reaction mixture is charged with vanadium (e.g., $V_2O_5$)

3.16 The method of 3.15, wherein the amount of vanadium is from 0.1%-0.5% by wt. with respect to the nonanal (e.g., 0.3% by wt. with respect to nonanal).

3.17 Any of the preceding methods, wherein the mixture is heated anywhere from 50° C.-100° C. (e.g., 60° C.) and then sparged with air.

3.18 Any of the preceding methods, wherein the mixture is heated anywhere from 50° C.-100° C. (e.g., 60° C.) and then sparged with oxygen.

The approaches disclosed herein can be very generally applied to a wide range of both aldehydes and ozonides formed from ozonolysis reactions according to any of Method 1.0 et seq, or any of Method 2.0 et seq, or any of Method 3.0 et seq. For example, unsaturated fatty alcohols, acids, and esters such as oleyl alcohol, oleic acid, oleic acid methyl ester, monounsaturated C6-C22 dioic acids and/or their ester derivatives, monounsaturated C6-C22 diols and/or their ester derivatives, monounsaturated C6-C22 acids and/or their ester derivatives, monounsaturated C6-C22 alcohols, and/or their ester derivatives, and any monounsaturated C6-C22 alkanes can be ozonized and then oxidized to generate mixtures of carboxylic acids and/or ketones.

In a further aspect, the invention encompasses treating oleyl alcohol or its ester with ozone, in the presence of either an acid or an alcohol, and subsequently quenched to generate mixtures of acid, alcohol, and ester. In one aspect, this mixture can be distilled to remove volatile components, and then can be further reactively distilled to drive-off any more volatile ester components, including nonanoic acid, resulting in high-quality 9-hydroxynonanoic acid polymer. This approach is more facile then other routes to 9-hydroxynonanoic acid polymer (see 'WO 2015027341 A1', 'Polymer Chemistry 2014, 5(9), 3203-3213', 'Biomacromolecules 2008, 9(3), 949-953', and 'Journal of Organic Chemistry 1960, 25, 108-111') and works exceedingly well when $V_2O_5$ is used in the quenching and aldehyde oxidation steps. For example, one aspect of this Method encompasses Scheme 1, as detailed below Scheme 1 comprises:

SCHEME 1.

R' = H or a fatty ester, R" = H or a fatty alkyl group

The above Scheme 1 details one process for making 9-hydroxynonanoic and its polymers from oleyl alcohol, and can be incorporated with any of Method 3.0, et seq.

The choice of solvent for the conversion of oleyl alcohol has a bearing on the products formed. Of course water can be used, but oleyl alcohol and water are immiscible and therefore the reaction would be carried out as an emulsion. If a homogenous solution is desired, acids and alcohols such as nonanoic acid, propanoic acid, acetic acid, and butanol would work well, to name a few. The alcohol or acid functionality will to a limited extent participate in the reaction, however, generating the corresponding esters with the alcohol and acid functionalities from nonanoic acid and 9-hydroxynonanoic acid. Fortunately, these esters can be exchanged during the final reactive distillation step to rectify the mixture and recover the solvent.

The reactive distillation can proceed at high temperature and reduced pressure, with or without catalyst. Lewis acid or Bronsted Acid catalysts can be used to good effect. In particular, cationic exchange resins such as Amberlyst, or tin catalysts such as the ones from the Reaxis™ series of catalysts would work well.

The products derived from the ozonolysis of oleyl alcohol can be used in a wide variety of applications, but are uniquely advantageous for use in cosmetics and personal care where features such as biocompatibility and renewability are highly valued.

In certain aspects, the invention encompasses Method 4.0, which comprises a method of making mixtures of acids, alcohols, and/or esters (e.g., 9-hydroxynonanoic acid), wherein the method comprises the ozonolysis of oleyl alcohol in the presence of either an acid or an alcohol, and wherein the products of that reaction are subsequently quenched.

In certain aspects, Method 4.0 encompasses the following:

4.1 The method of Method 4.0, wherein the ozonolysis is followed by an oxidative work-up where a metal is used as a catalyst.

4.2 The method of 4.1, wherein the metal is selected from manganese, molybdenum, and vanadium.

4.3 The method of any of the preceding methods, wherein the metal catalyst is vanadium pentoxide.

4.4 The method of any of the preceding methods, where the metal catalyst (e.g., vanadium pentoxide) is first used to quench ozonides and peroxide, and is then used to oxidize aldehydes to acids in the presence of a metal catalyst and oxygen or air.

4.5 The method of any of the preceding methods where an alcohol or carboxylic acid is used as a solvent in the ozonolysis and any esters that form from them are subsequently removed through reactive distillation (e.g., in some aspects a Lewis acid or Bronsted Acid may be used as catalysts).

4.6 The method of any of the preceding methods, wherein oleyl alcohol or its ester is treated with ozone, in the presence of either an acid or an alcohol, and subsequently quenched to generate mixtures of acid, alcohol, and ester.

4.7 The method of 4.6, wherein the mixture can be distilled to remove volatile components, and then can be further reactively distilled to drive-off any more volatile ester components, including nonanoic acid, resulting in high-quality 9-hydroxynonanoic acid polymer.

4.8 The method of any of the preceding methods, comprising the reaction detailed in Scheme 1.

4.9 The method of any of the preceding methods, wherein the method comprises a making 9-hydroxynonanoic acid from the ozonolysis of oleyl alcohol.

4.10 Any of the preceding methods, wherein the reaction mixture is charged with vanadium (e.g., $V_2O_5$)

4.11 The method of 1.24, wherein that amount of vanadium is from 0.1%-0.5% by wt. with respect to the oleyl alcohol (e.g., 0.3% by wt. with respect to oleyl alcohol).

4.12 Any of the preceding methods, wherein the mixture is heated anywhere from 10° C.-100° C. (e.g., 60° C.) and then sparged with air and/or 03.

The invention also contemplates any compounds that are obtained or obtainable from any of Method 1.0 et seq, Method 2.0, et seq, Method 3.0 et seq, or Method 4.0 et seq. A compound obtained from any of Method 1.0 et seq, Method 2.0, et seq, Method 3.0 et seq, or Method 4.0 et seq, can be used as fragrance composition, perfume, soap, candle composition, cosmetic composition, lubricant, and as a flavoring or flavorant, either as the sole ingredient or as part of a combination of ingredients.

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below. All percentages used herein, unless otherwise indicated, are by volume.

In the present specification, the structural formula of the compounds represents a certain isomer for convenience in some cases, but the present invention includes ail isomers, such as geometrical isomers, optical isomers based on an asymmetrical carbon, stereoisomers, tautomers, and the like. In addition, a crystal polymorphism may be present for the compounds represented by the formulas described herein, it is noted that any crystal form, crystal form mixture, or anhydride or hydrate thereof is included in the scope of the present invention.

All ratios used herein, unless otherwise indicated, are by molarity.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion.

Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" or "encompassing" is not intended to be limiting and is used in the same way that the term "comprising" is commonly used.

In some formulae of the present application, one or more chiral centers are identified by an asterisk placed next to the chiral carbon. In other formulae, no chiral center is identified, but the chiral isomers are nonetheless covered by these formulae.

Some compounds of the present invention can exist in a tautomeric form which is also intended to be encompassed within the scope of the present invention.

"Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, Li+, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group typically although not necessarily containing 1 to about 12 carbon atoms, such as methyl, ethyl, n-propyl, isopropyl, n-butyl, isobutyl, t-butyl, octyl, and the like.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like.

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

In at least one aspect, the methods described herein (e.g., Method 1.0 et seq, Method 2.0, et seq, Method 3.0 et seq, or Method 4.0 et seq) utilize structured reactors or packed tubes. And any compound obtained from any of Method 1.0 et seq or Method 2.0 et seq, Method 3.0 et seq, or Method 4.0 et seq) can be obtained by utilizing a structured reactor or packed tube. In certain aspect "packed bed reactors" can be used. These reactors are tubular and in some aspects are filled with solid catalyst particles, and can be used to catalyze gas reactions. At least one advantage of using a packed bed reactor can be the higher conversion per weight of catalyst than other catalytic reactors. The conversion is based on the amount of the solid catalyst rather than the volume of the reactor.

As used herein, the term "fragrance composition" means a mixture of fragrance ingredients, e.g., compounds that are obtained or obtainable from any of e.g., Method 1.0 et seq, Method 2.0, et seq, Method 3.0 et seq, or Method 4.0 et seq, including auxiliary substances if desired, dissolved in a suitable solvent or mixed with a powdery substrate used to provide a desired odor to a product.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furans, ketals, nitriles, acids, and hydrocarbons, including both saturated and unsaturated compounds and aliphatic carbocyclic and heterocyclic compounds, and animal products.

Fragrance and ingredients and mixtures of fragrance ingredients that may be used in combination with the disclosed compounds (e.g, a compound obtained by any of e.g., Method 1.0 et seq, Method 2.0, et seq, Method 3.0 et seq, or Method 4.0 et seq) for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

Invention also contemplates the method of using a compound obtained by any of e.g., Method 1.0 et seq, Method 2.0, et seq, Method 3.0 et seq, or Method 4.0 et seq, in a composition selected from the following: a fragrance composition, perfume, soap, lubricant and as a flavoring or flavorant.

In some embodiments, the product of the method of the invention may contain more than about 80% of any compound obtained by Method 1.0 et seq., or any compound obtained by Method 2.0 et seq, or Method 3.0 et seq, or Method 4, et seq. In some embodiments, the product of the method of the invention (e.g., any compound obtained by e.g., Method 1.0 et seq, Method 2.0, et seq, Method 3.0 et seq, or Method 4.0 et seq) may contain more than about 85%, more than about 90%, more than about 92%, more than about 95%, more than about 97%, more than about 98%, more than about 98.5%, or more than about 99%. In accordance with the aspects of the invention discussed herein, the product (e.g., any compound obtained by e.g., Method 1.0 et seq, Method 2.0, et seq, Method 3.0 et seq, or Method 4.0 et seq) may contain less than about 20%, less than about 15%, less than about 10%, less than about 8%, less than about 3%, less than about 2%, less than about 1.5%, or less an about 1% impurities.

In accordance with these embodiments, the product (e.g., any compound obtained by e.g., Method 1.0 et seq, Method 2.0, et seq, Method 3.0 et seq, or Method 4.0 et seq) may contain less than about 20%, less than about 15%, less than about 10%, less than about 8%, less than about 3%, less than about 2%, less than about 1.5%, or less an about 1% impurities.

As used herein, "perfume composition" means a mixture of fragrance materials, including auxiliary substances if desired, dissolved in a suitable solvent or mixed with a powdery substrate used to impart a desired odor to a product. In one aspect, "perfume compositions" described herein can comprise any compound obtained by e.g., Method 1.0 et seq, Method 2.0, et seq, Method 3.0 et seq, or Method 4.0 et seq. In a further aspect, any of the any compound obtained by e.g., Method 1.0 et seq, Method 2.0, et seq, Method 3.0 et seq, or Method 4.0 et seq, can be used as part of any of the foregoing examples of products having perfume compositions which include, but are not limited to, perfumes, soaps, detergents, air fresheners, room sprays, pomanders, candles, cosmetics, such as creams, ointments, toilet waters, pre- and aftershave lotions, talcum powders, hair-care agents, body deodorants and anti-perspirants. Fragrance materials and mixtures of fragrance materials that may be used in combination with the disclosed compounds for the manufacture of a perfume compositions include, but are not limited to, natural products including essential oils, absolutes, resinoids, resins, and concretes, and synthetic fragrance materials which include, but are not limited to, hydrocarbons, alcohols, aldehydes, ketones, ethers, acids, esters, acetals, ketals, and nitriles, including both saturated and unsaturated compounds and aliphatic carbocyclic and heterocyclic compounds.

Examples of the fragrance materials which may be used in combination with the disclosed (e.g., a compound obtained by any of e.g., Method 1.0 et seq, Method 2.0, et seq, Method 3.0 et seq, or Method 4.0 et seq) include but are not limited to, geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenylcarbinyl acetate, p-tert-butylcyclohexyl acetate, isononyl acetate, vetiveryl acetate, vetiverol, alphahexylcinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks.

Auxiliary substances and solvents which may be used in perfume compositions containing compounds according to the present invention include, but are not limited to, ethanol, isopropanol, dipropylene glycol, dipropyleneglycol monomethyl ether, and diethylphthalate.

The quantities of the disclosed compounds used in a fragrance or perfume or cosmetic composition or a product to be perfumed may vary according to the nature of the product, the nature and quantity of the other fragrance materials in the flavor, fragrance, perfume, soap, or cosmetic composition, and on the desired odor effect. For example, any compound obtained by e.g., Method 1.0 et seq, Method 2.0, et seq, Method 3.0 et seq, or Method 4.0 et seq may be found in a given flavor, fragrance, perfume, soap, or cosmetic composition from 0.005% to 25%, by weight of the composition, from 0.05% to 10%, by weight of the composition, or more particularly, from 0.1% to 5% by weight of the composition.

EXAMPLES

Example 1: Nonanal Oxidation to Nonanoic Acid Using Air

Nonanal (43.0 g, 0.3 mol) is diluted with acetic acid to a volume of 200 ml. The reaction mixture is then charged with 130 mg of $V_2O_5$ (0.3% by wt. with respect to nonanal). The mixture is then heated to 60° C. and was sparged with air. After 6 hours of reaction there appears to be a 6.4:1 ratio of nonanoic acid to nonanal by GC FID.

Example 2: Nonanal Oxidation to Nonanoic Acid Using Oxygen

Nonanal (41.5 g, 0.29 mol) is diluted with acetic acid to a volume of 200 ml. The reaction mixture is then charged with 130 mg of $V_2O_5$ (0.3% by wt. with respect to nonanal). The mixture is then heated to 60° C. and was sparged with oxygen. After 80 minutes of reaction there appears to be a 76.1:3.5 ratio of nonanoic acid to nonanal by GC FID.

Example 3: Methoxymelonal Oxidation to Methoxymelonic Acid

Methoxymelonal (20 g, 0.116 mol) is dissolved into 90 ml of acetic acid. The reaction mixture is then charged with 100 mg of $V_2O_5$ (0.3% by wt. with respect to methoxymelonal). The mixture is then heated to 60° C. and was sparged with oxygen. After 80 minutes of reaction there appears to be a 41:36 ratio of methoxymelonic acid to melonal by GC FID.

Example 4: Comparing Different Catalysts in the Conversion of Nonanal to Nonanoic Acid To generate conversion data for FIG. 1, a standardized set of conditions is used. Nonanal, 60 g, neat, is charged with 120 mg of inorganic catalyst in a round-bottomed flask, except for the control where no catalyst is used. The reaction mixture is then placed in a oil bath kept at 70-80° C. and is outfitted with an oxygen sparger that keeps oxygen sparging through the solution at a rolling boil. A sample is taken every 20 minutes and was analyzed by GC FID. All conversion data is based on GC conversion and purity, which is corroborated with $^1H$ NMR where possible.

Example 5: Ozonolysis of Oleyl Alcohol to Generate Nonanoic Acid and 9-Hydroxynonanoic Acid Oleyl alcohol (100 ml) is dissolved in propanoic acid (200 ml) in a jacketed reactor equipped with a gas sparger and an overhead stirrer. The reaction mixture is cooled to 10° C. while stirring and an $O_3$/air mixture is sparged through the reactor over the course of 100 minutes until all olefin has been consumed, making sure that the internal temperature does not exceed 15° C. The peroxide value of the mixture is tested using iodometric titration and is calculated to be 450 mmol/L.

This mixture is then pumped through a ¼" OD tube packed with sand mixed with 5% by wt. $V_2O_5$ that is kept at 90° C. The flow rate is established such that the residence time in the packed tube is less than 15 minutes. After the material has passed through the tube, another peroxide test is performed the peroxide value was calculated to be 40 mmol/L.

Figure 2:
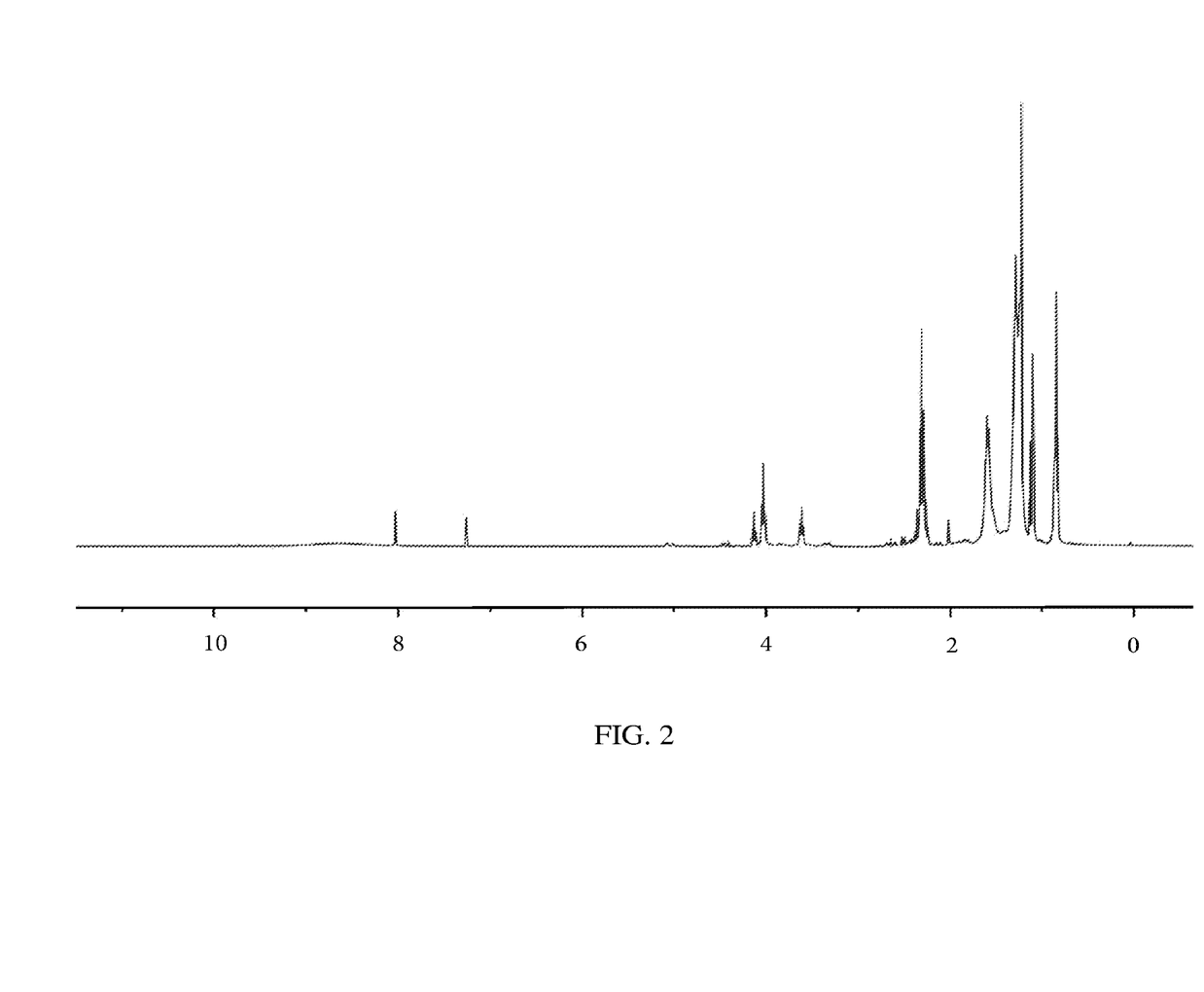
FIG. 2. $^1$H NMR for the mixture of nonanoic acid, 9-hydroxynonanoic acid, and their corresponding esters.
Figure 3:
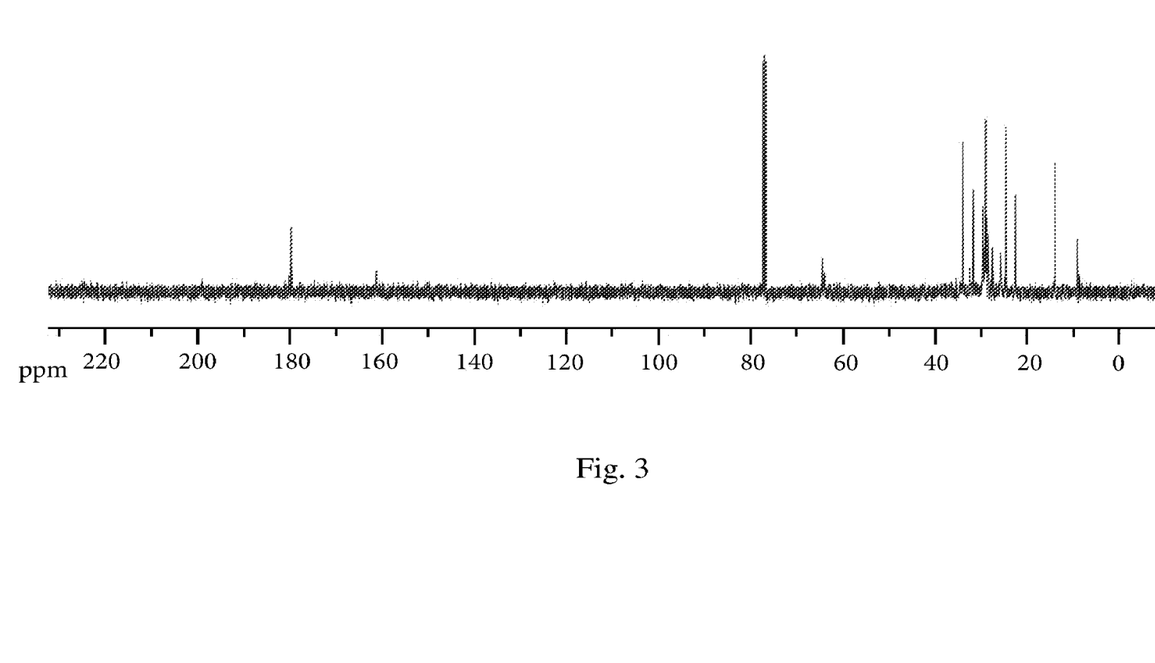
FIG. 3. $^{13}$C NMR for the mixture of nonanoic acid, 9-hydroxynonanoic acid, and their corresponding esters.

This mixture is then collected, charged with 250 mg of $V_2O_5$, and is sparged with oxygen at between 70 and 80° C. for several hours until $^1H$ NMR shows no more aldehyde peak to be present. Finally, the propanoic acid solvent is removed via distillation, resulting in a mixture of nonanoic acid, 9-hydroxynonanoic acid, and corresponding esters. The NMR data for this mixture is provided in FIG. 2. The resulting mixture from Example 5 (86 g) is charged with Amberlyst™ cationic resin beads (~2 g) and is distilled at reduced pressure 0.5-2 mbar and 100° C. for 4 hours.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

The invention claimed is:

1. A method of oxidizing aldehydes to acids, comprising the steps of:
providing vanadium to oxidize aldehydes to carboxylic acids in the presence of air or oxygen at a predetermined temperature range in an acidic solvent, wherein the aldehydes are aliphatic alkyl aldehydes or oxo analogs thereof, aromatic aldehydes, or terpene aldehydes, and wherein the oxidant is air or oxygen gas.

2. The method of claim 1, wherein said acidic solvent comprises acetic acid.

3. The method of claim 1, wherein said acidic solvent comprises a carboxylic acid selected from formic, propanoic, butanoic, pentanoic, hexanoic, heptanoic, octanoic, nonanoic, decanoic, dodecanoic, palmitic, and stearic acid.

4. The method of claim 1, wherein said vanadium comprises vanadium pentoxide.

5. The method of claim 1, wherein said aldehydes comprise C3 to C15 optionally functionalized linear alkyl aldehydes and said carboxylic acids comprise C3 to C15 optionally functionalized linear alkyl carboxylic acids.

6. The method of claim 1, wherein said aldehyde is hydroxycitronellal and said carboxylic acid is hydroxycitronellic acid.

7. The method of claim 1, wherein said aldehyde is methoxymelonal and said carboxylic acid is methoxymelonic acid.

8. The method of claim 1, wherein said aldehyde is hydroxymelonal and said carboxylic acid is hydroxymelonic acid.

9. The method of claim 1, wherein said aldehyde is methoxycitronellal and said carboxylic acid is methoxycitronellic acid.

10. The method of claim 1, wherein said aldehydes are aromatic aldehydes and said carboxylic acids are aromatic carboxylic acids.

11. The method of claim 1, wherein said aldehyde is 9-oxononanol and said acid is 9-hydroxynonanoic acid.

12. A method of oxidizing a mixture of ozonides and aldehydes, comprising the steps of:
providing vanadium to oxidize mixtures of ozonides and aldehydes to carboxylic acids in the presence of air or oxygen at a predetermined temperature range in an acidic solvent, wherein said ozonides are derived by ozonolysis from an unsaturated fatty monoacid, diacid, monoester, diester, diol, or alcohol, wherein the oxidant is air or oxygen gas.

13. A method of oxidizing an ozonide mixture, comprising the steps of:
providing vanadium to oxidize mixtures of ozonides to ketones, carboxylic acids, or mixtures thereof in the presence of air or oxygen at a predetermined temperature range in an acidic solvent, wherein said ozonides are derived by ozonolysis from an unsaturated fatty monoacid, diacid, monoester, diester, diol, or alcohol, and wherein the oxidant is air or oxygen gas.

14. The method according to claim 13, wherein the method comprises the steps of reacting oleyl alcohol with ozone to form the ozonides, and oxidizing the ozonides with vanadium to provide 9-hydroxynonanoic acid.

15. The method of claim 14 wherein the vanadium is vanadium pentoxide.

16. The method of claim 14, wherein the vanadium is used to quench the ozonides and/or any peroxides, and is used to oxidize initially formed aldehydes to the 9-hydroxynonanoic acid.

17. The method according to claim 1, wherein the aldehyde is nonanal, and the nonanal is oxidized to nonanoic acid using vanadium and air or oxygen.

18. The method according to claim 13, wherein said ozonides are derived by ozonolysis from an unsaturated fatty alcohol.

19. The method according to claim 13, wherein the ozonide mixture is continuously passed through a structured reactor or packed tube containing the vanadium.

20. The method according to claim 11, wherein the method further comprises the oxidation the 9-hydroxynonanoic acid to form the diacid azelaic acid.

21. The method according to claim 14, wherein the method further comprises the oxidation the 9-hydroxynonanoic acid to form the diacid azelaic acid.

* * * * *